US012636114B2

(12) United States Patent
Guzik et al.

(10) Patent No.: US 12,636,114 B2
(45) Date of Patent: May 26, 2026

(54) SURGICAL LIGHTING

(71) Applicant: LUMITEX, INC., Strongsville, OH (US)

(72) Inventors: Carolyn Guzik, Strongsville, OH (US); Michael Kerns, Strongsville, OH (US); Nicolette Diehl, Brunswick, OH (US); Jessica Quartermaine, Medina, OH (US); Heather Allen, Cleveland, OH (US); Alan Greszler, Strongsville, OH (US)

(73) Assignee: Lumitex, Inc., Brecksville, OH (US)

( * ) Notice: Subject to any disclaimer, the term of this patent is extended or adjusted under 35 U.S.C. 154(b) by 37 days.

(21) Appl. No.: 18/712,023

(22) PCT Filed: Oct. 14, 2022

(86) PCT No.: PCT/US2022/078116
§ 371 (c)(1),
(2) Date: May 21, 2024

(87) PCT Pub. No.: WO2023/107774
PCT Pub. Date: Jun. 15, 2023

(65) Prior Publication Data
US 2025/0017684 A1     Jan. 16, 2025

Related U.S. Application Data

(60) Provisional application No. 63/288,005, filed on Dec. 10, 2021.

(51) Int. Cl.
*A61B 90/30*     (2016.01)
*A61B 90/35*     (2016.01)
(Continued)

(52) U.S. Cl.
CPC .............. *A61B 90/30* (2016.02); *F21V 14/00* (2013.01); *F21V 14/003* (2013.01);
(Continued)

(58) Field of Classification Search
CPC ............ A61B 90/30; A61B 2562/0257; A61B 90/35; G16H 40/63; F21V 23/0435;
(Continued)

(56) References Cited

U.S. PATENT DOCUMENTS

| | | | | |
|---|---|---|---|---|
| 10,544,921 | B2 * | 1/2020 | Li | ......................... F21V 14/003 |
| 2007/0041167 | A1 * | 2/2007 | Nachi | ..................... F21V 17/02 |
| | | | | 362/241 |

(Continued)

FOREIGN PATENT DOCUMENTS

| | | |
|---|---|---|
| DE | 102011007201 A1 | 5/2012 |
| WO | 2004080291 A2 | 9/2004 |

OTHER PUBLICATIONS

Machine translate of WO 2019/0241996 A1 (Dec. 26, 2019) (Year: 2019).*

(Continued)

*Primary Examiner* — Laura K Tso
(74) *Attorney, Agent, or Firm* — Renner, Otto, Boisselle & Sklar, LLP

(57)     ABSTRACT

A medical illumination system is provided for modulating properties of light emitted by a light source of the illumination system based on properties of a spot size defining an area illuminated by the emitted light.

16 Claims, 3 Drawing Sheets

(51) Int. Cl.
    *F21V 14/00*       (2018.01)
    *F21V 23/04*       (2006.01)
    *F21W 131/205*    (2006.01)
    *G16H 40/63*      (2018.01)

(52) U.S. Cl.
    CPC ........ *F21V 14/006* (2013.01); *F21V 23/0435*
          (2013.01); *F21V 23/0464* (2013.01); *G16H*
        *40/63* (2018.01); *A61B 90/35* (2016.02); *A61B*
            *2562/0257* (2013.01); *F21W 2131/205*
                           (2013.01)

(58) Field of Classification Search
    CPC ............... F21V 23/0464; F21V 14/00–14/085;
                                  F21W 2131/205
    USPC ........................................................ 362/572
    See application file for complete search history.

(56)                    References Cited

U.S. PATENT DOCUMENTS

| 2017/0367785 A1 | 12/2017 | Munari |
| 2019/0249847 A1 | 8/2019 | Hallack et al. |

OTHER PUBLICATIONS

International Search Report and Written Opinion (ISRWO) corresponding to counterpart International Patent Application PCT/US2022/078116 mailed Mar. 16, 2023.

\* cited by examiner

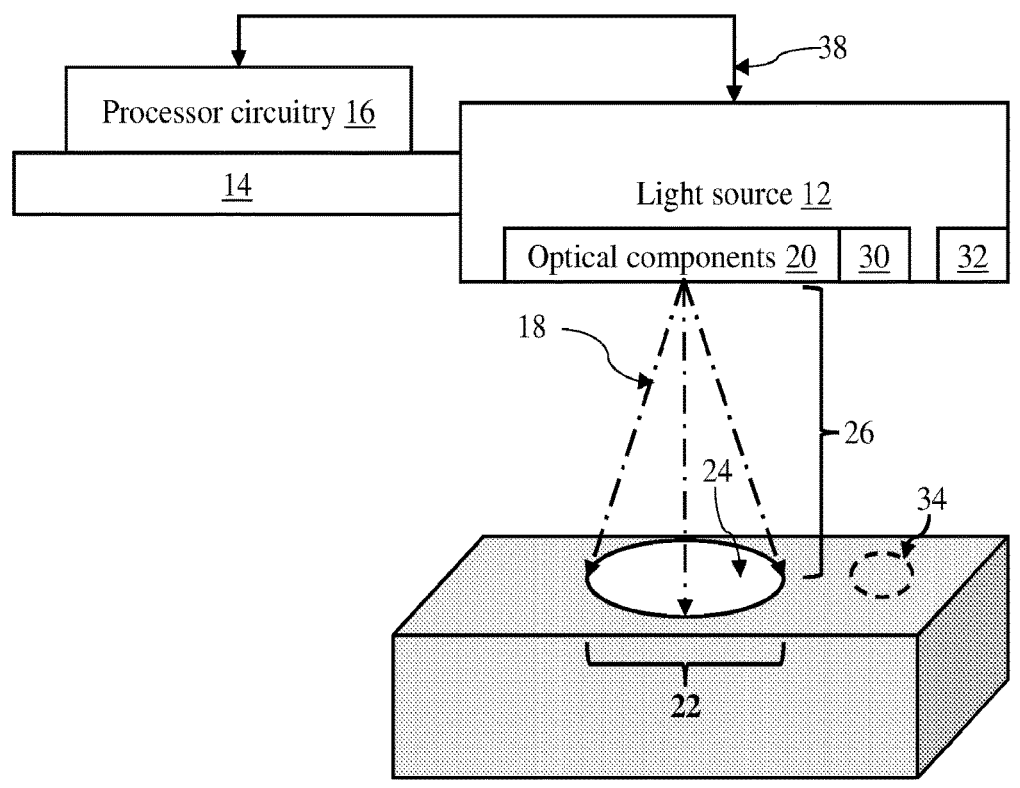
FIG. 1
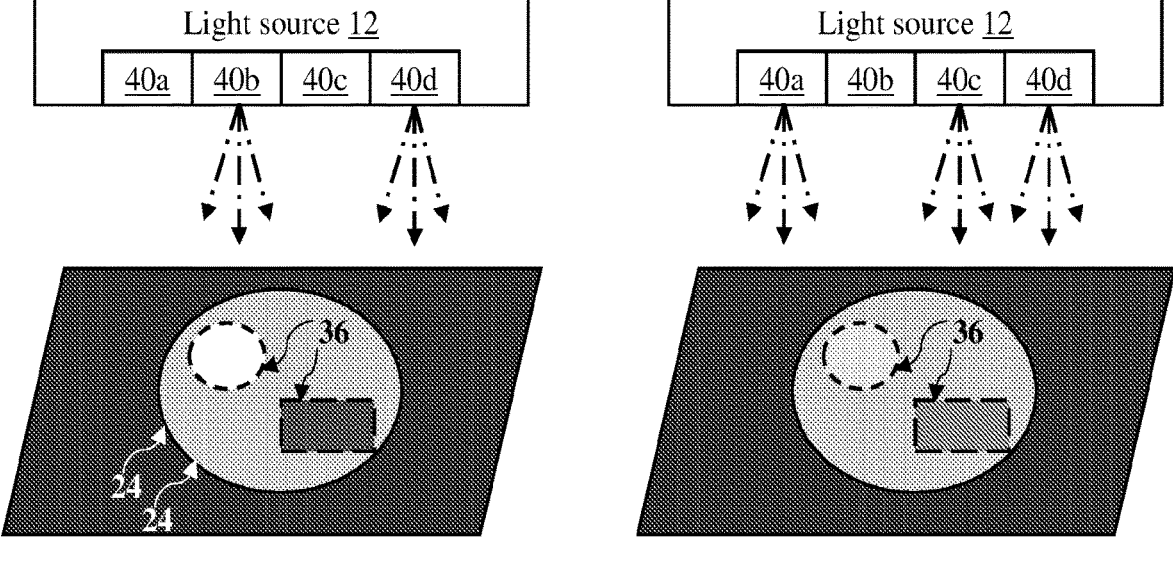
FIG. 2                                                              FIG. 3

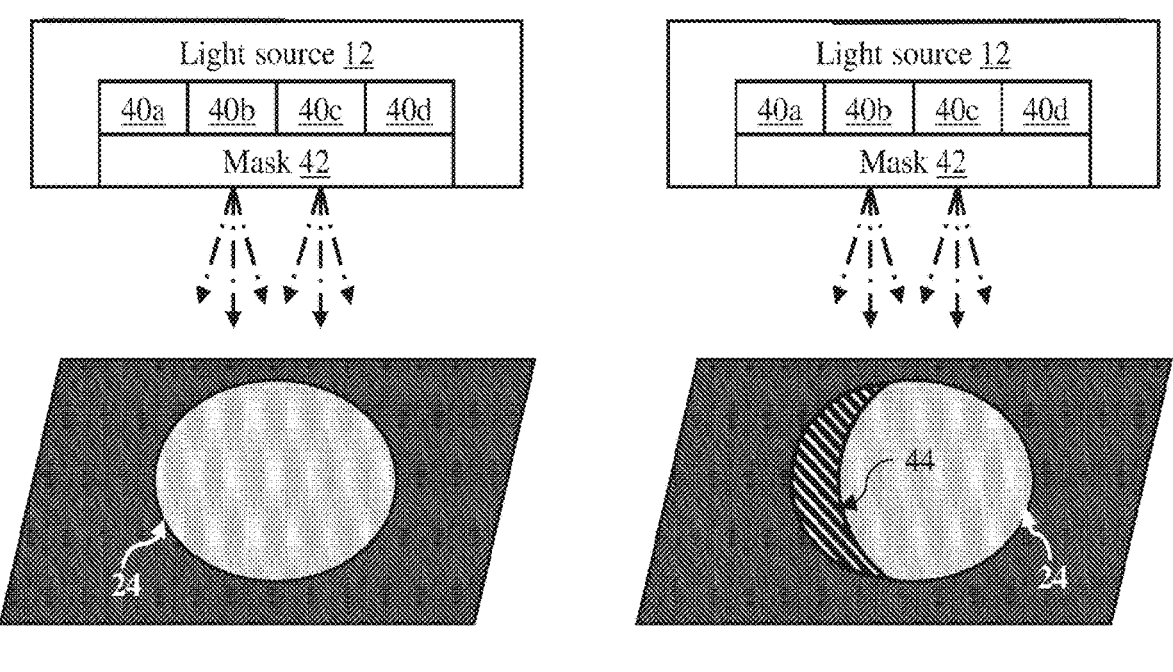
FIG. 4                    FIG. 5
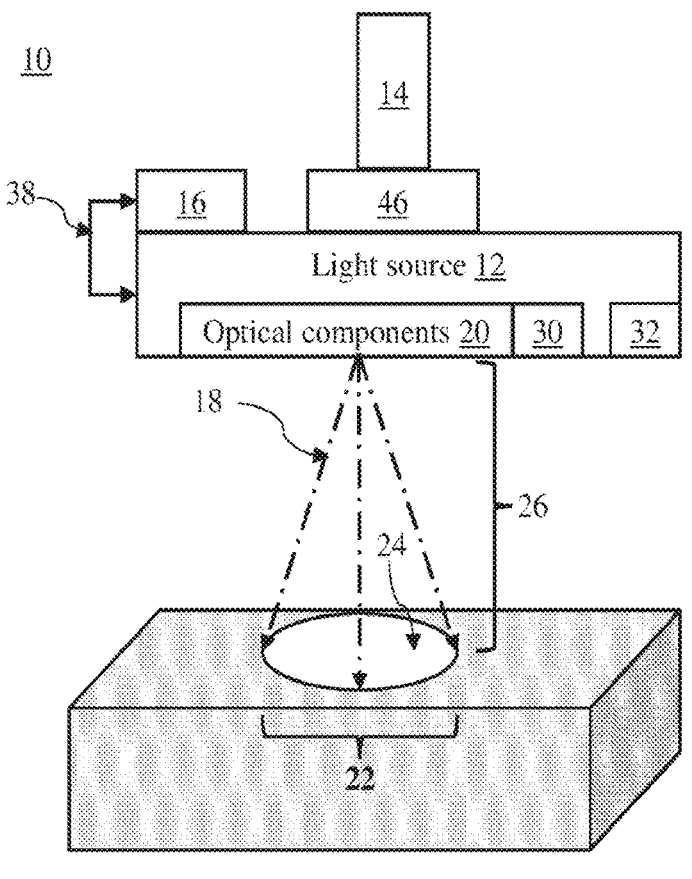
FIG. 6

SURGICAL LIGHTING

RELATED APPLICATIONS

This application is a national phase of International Application No. PCT/US2022/078116 filed Oct. 14, 2022, which claims priority to United States of America Application No. 63/288,005 filed on Dec. 10, 2021, each of which is herein incorporated by reference in its entirety.

TECHNICAL FIELD

The present disclosure relates generally to medical lighting and more particularly to lighting in labor and delivery rooms.

BACKGROUND

Surgical performance in the operating room is to an extent dependent upon effective illumination of the surgical area. Effective illumination is equally important in labor and delivery rooms. Effective medical illumination (1) centers on the doctor's immediate field, (2) illuminates a wide or narrow field with high-intensity light, and (3) minimizes shadows caused by obstructions. Another goal of effective medical illumination is to reduce shadow, glare, and artifacts in visualization of the field of interest.

Efficacious medical illumination combines sufficient ambient light with the ability to apply focused light at specific operative stages and angles. Rather than merely applying brighter light, a nuanced approach balances the negative effects caused by brighter light (e.g., glare, eye strain, etc.).

There are currently three predominant methods of illumination utilized in the medical field: operating room lights, lighted retractors, and headlights. For traditional labor and delivery rooms, standard operating room lights are broadly used to illuminate the operating room during procedures. Lighted surgical retractors provide in-field focused illumination targeted to a surgical or operation site. Medical personnel may also wear headlights to improve mobility and manipulation of the light field.

SUMMARY

The present disclosure provides improved illumination systems for use in labor and delivery rooms, operating rooms, etc. by modulating properties of a spot size defining an area illuminated by the light emitted by the illuminating system.

While a number of features are described herein with respect to embodiments of the invention; features described with respect to a given embodiment also may be employed in connection with other embodiments. The following description set forth certain illustrative embodiments of the invention. These embodiments are indicative, however, of but a few of the many ways in which the principles of the invention may be employed. Other objects, advantages, and novel features according to aspects of the invention will become apparent from the following detailed description.

BRIEF DESCRIPTION OF THE DRAWINGS

The annexed drawings, which are not necessarily to scale, show various aspects of the invention in which similar reference numerals are used to indicate the same or similar parts in the various views.

FIG. 1 is a schematic view of an exemplary embodiment of a medical illuminating system including a light source.

FIG. 2 is a schematic view of the medical illuminating system having a light source with multiple light emitters, and an illuminated area including an illumination anomaly.

FIG. 3 is a schematic view of the illuminated area of FIG. 2 with the illumination anomaly mitigated.

FIG. 4 is a schematic view of a light source having a mask and an illuminated area.

FIG. 5 is a schematic view of the illuminated area of FIG. 6 having a masked region.

FIG. 6 is a schematic view of an exemplary embodiment of the medical illuminating system including an actuator.

Figure 7:
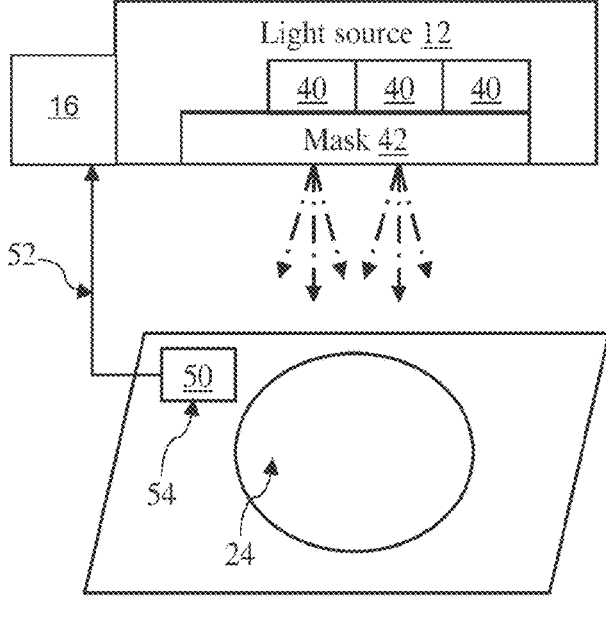
FIG. 7 is a schematic view of an exemplary embodiment of the medical illuminating system including a remote control.

The present invention is described below in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

DETAILED DESCRIPTION

To improve illumination in labor and delivery rooms, various components described below may be used alone or in combination.

According to a general embodiment, an illumination system is presented including one or more light source for emitting electromagnetic radiation and processor circuitry 16 for modulating properties of the emitted electromagnetic radiation.

Turning to FIG. 1, an exemplary medical illuminating system 10 is shown for illuminating a work area (also referred to as a surgical work area). The system 10 includes a light source 12, a mount 14, and processor circuitry 16. The light source 12 emits light 18 (also referred to as electromagnetic radiation) and includes optical components 20 for modulating properties of a spot size 22 of the emitted light 18. The mount 14 mechanically supports and maintain a position of the light source 12. The processor circuitry 16 modulates properties of the spot size 22 defining an area 24 illuminated by the emitted light 18 (referred to as the illuminated area). The modulated properties of the light source 12 may include at least one of position of the illuminated area, size (e.g., diameter) of the illuminated area 24 (also referred to as the illumination field), focus setting of the optical components 20, and brightness of the illuminated area 24.

For example, the optical components 20 may include a focus mechanism (e.g., deformable lenses or mirrors) for adjusting the size of the illuminated area 24 (also referred to as spot size). The processor circuitry 16 may be configured to control the focus mechanism and/or light sources. The focus mechanism may include at least one of a liquid lens or Gradient-Index (GRIN) Lens for modulating the spot size.

In one embodiment, the focus mechanism does not utilize mechanical movement for adjusting the spot size. For example, the focus mechanism may use focusing and beam directing for adjusting the spot size without mechanical movement. In another example, the processor circuitry 16 may control beam angle of the light source 16. For example, the optical components 20 may include a liquid crystal (LC) beam shaper for modulating the beam angle of light emitted by the light source 12.

The processor circuitry 16 may control operation of the focus mechanism to eliminate jitter in the focus caused by movement. For example, the processor circuitry 16 may utilize a tuned proportional-integral-derivative (PID) controller or a machine learning algorithm to mitigate the effect of noisy movement (i.e., as opposed to intentional movement involved in focusing).

The processor circuitry 16 may compensate for a working distance 26 of the light source 12 by maintaining at least one of an area of the spot size 22, a brightness of the spot size 22, a position of the spot size 22, or a pattern of the spot size 22. The working distance 26 is a distance between the light source 12 and an area 28 illuminated by the emitted light 18. For example, the processor circuitry 16 may use time of flight to measure the working distance and adjust the focus based on the measured working distance.

In one embodiment, the system 10 includes a distance sensor 30 for measuring a distance between the illuminated area 24 and the light source 12. The distance sensor 30 may be any suitable non-contact sensor for measuring distance such as an ultrasonic or light based sensor. The processor circuitry 16 may receive a measurement of the working distance 26 from the distance sensor 30 and modulate properties of the light source 12 based on the measured working distance. For example, the spot size may be maintained at a desired size (e.g., 10 inches) independent from the working distance (e.g., 75 inches, 150 inches, etc.).

As an example, based on known properties of the light source 12, the processor circuitry 16 may determine (e.g., using a lookup table) properties of the illuminated area 24 from the measured working distance. As an example, based on a focus setting of the light source 12 and the measured working distance, the processor circuitry 16 may determine a size (e.g., area or diameter) of the spot size 22. The processor circuitry 16 may also modulate properties of the light source 12 (e.g., adjusting the focus setting of the light source 12), such that the properties of the illuminated area 24 fall within a received acceptable range (e.g., the diameter of the spot size 22 is approximately equal to a specific size).

The system 10 may also include a photodetector 32 configured to measure properties of at least one of the spot size 22 or the ambient light brightness. For example, the photodetector 32 may measure at least one of the position, the brightness, the area, or the pattern of the spot size 22. The pattern of the spot size 22 may refer to a shape of the spot size 22 (e.g., elliptical, circular, square, rectangular, etc.). The processor circuitry 16 may be configured to modulate the light source 16 (e.g., the optical components 20), such that the measured spot size has the desired size or falls within a desired sized range. For example, the photodetector 32 may measure a brightness of a field of view to identify the illuminated area 24. As an example, the measured brightness may be a peak brightness an average brightness, or any other suitable measurement indicating a brightness of the entire illuminated area 24 or a portion of the illuminated area. The processor circuitry 16 may be configured to modulate the light sources, such that the measured brightness has the desired brightness or falls within a desired brightness range.

The ambient light brightness may be determined by measuring a brightness of a location 34 outside of the illuminated area 24. For example, the processor circuitry 16 may modulate the brightness of the emitted light 18 based on the ambient light brightness, such that a higher ambient light brightness corresponds to a higher brightness of the illuminated area. Alternatively or additionally, the processor circuitry 16 may modulate the brightness of the emitted light 18, such that the measured brightness falls within a desired brightness range.

The photodetector 32 may comprise any suitable sensor for measuring properties of the illuminated area 24. For example, the photodetector 32 may include a photosensor, camera, CCD camera, spectrometer, etc. The measured properties may include spot size, brightness, color, CRI, uniformity of illumination, correlated color temperature (CCT), etc. The photodetector 32 may also be mounted to any suitable structure. For example, the photodetector 32 may be mechanically supported by the light source 12 or the mount 14. In one embodiment, the photodetector 32 is included in the light source 12.

Turning to FIGS. 2 and 3, the processor circuitry 16 may also detect an illumination anomaly 36 in the illuminated area 24. The illumination anomaly 36 may be at least one of a glare or a shadow in the illuminated area 24. The illumination anomaly 36 may be detected based on an output of the photodetector 32. For example, the processor circuitry 16 may detect an increase or decrease in the brightness in an affect portion of the illuminated area 24. In one embodiment, any portion of the illuminated area 24 having a difference in brightness of more than an anomaly threshold (e.g., 10%, 20%, 30%, etc.) from an average brightness of the illuminated area may be defined as an illumination anomaly 36. The processor circuitry 16 may modulate properties of the light source 12, such that the detected illumination anomaly is mitigated. For example, the processor circuitry 16 may alter a driving current of the light source 12, adjust the focus setting of the light source 12, change a position of the light source 12, etc. As an example, movement of obstructions (e.g., people and equipment) may be detected and the light source may be reconfigured to compensate for this movement to mitigate shadows caused by the obstructions.

In the example depicted in FIGS. 2 and 3, the light source 12 includes multiple light emitters 40a, 40b, 40c, 40. In FIG. 2, light 18 is being emitted by light emitters 40b and 40d and is resulting in two illumination anomalies 36: a glare (represented by the lighter circle) and a shadow (represented by the darker rectangle). In FIG. 3, the processor circuitry 16 caused light emitter 40b to stop emitting light and caused light emitters 40a and 40d to start emitting light. This caused a reduction in the illumination anomalies (e.g., the brightness of the glare was reduced, and the brightness of the shadow was increased).

The processor circuitry 16 may modulate properties of the spot size by sending control signals 38 to the optical components 20 of the light source 12. The optical components 20 may modulate the properties of the spot size 22 based on the control signals 38 received from the processor circuitry 16.

The light source 12 may include light emitters 40 located at different spatial positions. For example, at least a portion of the light emitters 40 may be arranged in a grid or array. The processor circuitry 16 may control the properties of the spot size 22 without mechanical movement of the light source 12 by separately controlling properties of the light emitted by the light emitters 40. For example, a brightness of the light emitted by the light emitters 40 may be separately controlled (e.g., a portion of the light emitters 40 may not emit light). Similarly, the processor circuitry 16 may selectively control the light emitters 40 that are emitting light to affect properties of the illuminated area 24 without altering a focusing of the light 18.

Turning to FIGS. 4 and 5, the light source 12 may include a mask 42 for reducing transmission of the light 18 (i.e., reduce brightness) within a region of the illuminated area 24 referred to as a masked region 44. The mask 42 may be any suitable device for reducing (e.g., blocking) transmission of light. The processor circuitry 16 may control at least one of the location, size, or shape of the masked region 44. The processor circuitry 16 may control the properties of the masked region to achieve desired brightness within the masked region. For example, the mask comprises a liquid crystal filter or other light blocking material and the processor circuitry 16 may control transmission of light through pixels of the liquid crystal filter.

The optical components 20 may include any optical elements for affecting transmission of light 18 from the light source 18. For example, the optical components 20 may include at least one of a focus mechanism, an aperture, a diffraction grating, a mask, a lens, or a wavelength filter configured to alter a wavelength of the emitted electromagnetic radiation (e.g., one or more of an LCD, polymeric nanolayer, etc.).

In addition to the light source 12, the mount 14 may also mechanically support the processor circuitry 16. In one embodiment, the mount 14 includes a boom arm (also referred to as a swing arm). A position of the light source 12 may be adjustable relative to the boom arm.

The mount 14 may include any suitable hardware for physically maintaining the position of the light source(s). For example, the mount 14 may be portable for emergency situations, military deployment. In this example, the mount 14 may include lockable wheels that may be unlocked during movement. When the illumination system 10 is to remain stationary, the wheels may be locked, such that the mount 14 does not move.

In one embodiment, the mount 14 is attached to a ceiling of a room. The mount 14 may be fixed in location or moveable, such that the mount 14 moves across the ceiling. For example, the mount 14 may include a ball joint for moving the illuminated area. The mount 14 may include a slider that the light source 12 is mounted to. The light emitters 40 may be separately moveable along the slider to alter the illuminated area 24. In one embodiment, the mount 14 includes a z-axis translator. The z-axis translator may be configured to move light emitters along the z-axis to change a size of the illuminated area 24.

Turning to FIG. 6, the mount 14 may include an actuator 46 for controlling a position of the illuminated area 24 by adjusting at least one of a position or an angle of at least one of the light source 12 or the optical components 20. Alternatively or additionally, the light emitters 40 may be arranged in an array, such that the processor circuitry 16 may control (e.g., electronically) the position of the illuminated area 24 by controlling which of the light emitters 40 emit light (e.g., without mechanical movement of the light sources or focusing mechanism).

As shown in FIG. 7, the system 10 may also include a remote control 50 for sending remote control signals 52 to the processor circuitry 16. For example, the remote control may include a user interface (e.g., buttons, a touch screen, etc.) for receiving commands from the user that are passed to the processor circuitry 16 by the remote control. The remote control signals 52 may include at least one of a measurement location 54 based on a location of the remote control 50 or a measured brightness at the measurement location 54. The processor circuitry 16 may receive the remote control signals 52 from the remote control 50 and control the position of the illuminated area 24 based on the remote control signals 52, such that a center of the illuminated area 24 has a defined position relative to the measurement location 54. For example, the illuminated area may be centered at the measurement location. Alternatively or additionally, the processor circuitry 16 may control the brightness of the illuminated area 24 based on the remote control signals 52, such that the measured brightness at the location of the remote control is within a desired brightness range.

In one embodiment, the remote control includes a light sensor (e.g., a photosensor) configured to measure a brightness of received electromagnetic radiation. The remote control may be placed at a measurement location and the brightness of the measurement location may be sent to the processor circuitry 16. The position of the measurement location may be sent to the processor circuitry 16 or may be determined by the processor circuitry 16 (e.g., using a camera).

Figure 8:
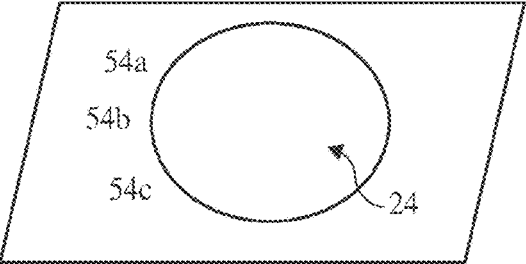
FIG. 8 is a schematic view of the illuminated area of FIG. 7 and multiple measurement locations.
Figure 9:
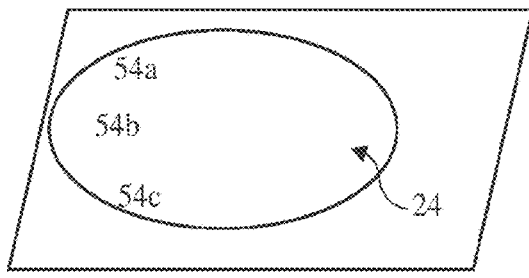
FIG. 9 is a schematic view of the illuminated area of FIG. 8 expanded to encompass and the multiple measurement locations.

In one embodiment, the remote control signals 52 include multiple measurement locations 54. For example, a first measurement location 54 is captured in FIG. 7. This measurement location is shown as 54a in FIG. 8. Also shown in FIG. 8, are measurement locations 54b and 54c which were similarly captured using the remote control 50. The processor circuitry 16 receives the multiple measurement locations 54 and modulates properties of the light source 16, such that a brightness at each of the multiple measurement locations falls within the desired brightness range. For example, in FIG. 9 the illuminated area 24 has been modified to include the measurement locations 54a, 54b, and 54c.

For example, the illumination system 10 may include a remote sensor (e.g., a camera) and the remote sensor may identify a location of the remote control each time a measurement location capture request is received by the processor circuitry 16. As an example, a user may push a capture button on the remote control 50 at each of the measurement locations 54. When the processor circuitry 16 receives a signal from the remote control indicating that the capture button has been pressed, the processor circuitry 16 may identify a location of the remote control at the time the capture button was pressed using the remote sensor. Each of these identified locations may be one of the multiple measurement locations.

The remote control may be any suitable device for sending information to the processor circuitry 16. For example, the remote control may be a sensor worn or positioned at a particular location and configured to transmit a measured brightness value to the processor circuitry 16. In another example, the remote control may be one or more cameras for receiving gesture controls from users and/or microphone(s) for receiving voice controls from users.

Once the multiple measurement locations have been received, the processor circuitry 16 may adjust at least one of the position, focus, and brightness of the illuminated area such that the brightness at each of the multiple measurement locations falls within a desired range. The brightness at each of the multiple measurement locations may be measured using the remote sensor.

The processor circuitry 16 may also control wavelengths contained in the emitted light 18 based on a received color profile. In one embodiment, the received color profile may include a duration, timing, and/or intensity of one or more wavelength ranges, such that an optical dose of wavelengths of light received by the illuminated area may be controlled by the processor circuitry 16. In one embodiment, the processor circuitry 16 receives a program of light properties identifying included wavelengths, intensity of included wavelengths, spot size, and brightness.

The light sources may be any suitable structure for emitting light. For example, the light sources may include one or more light emitting diodes (LEDs), organic LEDs (OLEDs), microLEDs, laser diodes, mini-LED, quantum dot (QD)-conversion, phosphor conversion, excimer lamps, halogen lamps, multi-photon combination, or SLM wavefront manipulation. The light sources may also emit any suitable wavelength, color rendering index (CRI), and color temperature of electromagnetic radiation. For example, the light sources may be controllable to modulate a wavelength of emitted electromagnetic radiation. In one embodiment, the light source includes at least one laser source to simplify collimation and to reduce potential temperature issues.

The light source may be mounted to any suitable structure. For example, as is described in further detail below, the light sources may be supported by a mount. As another example, the light sources may be attached to objects in the room (e.g., stirrups, rails, etc.).

The light source 12 may emit any suitable wavelength of light. For example, the light source 12 may include a filter for modifying wavelengths included in the emitted light. Alternatively or additionally, the light source 12 includes light emitters 40 that emit different wavelengths of light. The light source 12 may control the wavelengths included in the emitted light by controlling which of the light emitters emit light and the intensity of the light emitted by these light emitters.

The processor circuitry 16 may have various implementations. For example, the processor circuitry 16 may include any suitable device, such as a processor (e.g., CPU), programmable circuit, integrated circuit, memory and I/O circuits, an application specific integrated circuit, microcontroller, complex programmable logic device, other programmable circuits, or the like. The processor circuitry 16 may also include a non-transitory computer readable medium, such as random-access memory (RAM), a read-only memory (ROM), an erasable programmable read-only memory (EPROM or Flash memory), or any other suitable medium. Instructions for performing the method described below may be stored in the non-transitory computer readable medium and executed by the processor circuitry 16. The processor circuitry 16 may be communicatively coupled to the computer readable medium and network interface through a system bus, mother board, or using any other suitable structure known in the art.

In addition to illuminating an area for medical procedures (e.g., delivery a baby, performing a cesarean, etc.), the emitted electromagnetic radiation may be used for photobiomodulation or sterilization. For example, the emitted electromagnetic radiation may include ultraviolet (UV) light for killing germs and/or infrared light for wound healing.

In one embodiment, the control system is configured to cause the illumination system to illuminate at least a portion of the room in which the illumination system is located. For example, the control system may be configured to illuminate a portion of the room with a dose of electromagnetic radiation configured to sterilize the portion of the room. As an example, the illumination system may be used to sterilize the room when the room is not in use. For example, the illumination system may include a person detector (e.g., a thermal camera or motion sensor) configured to detect when the room is empty. The control system may be configured to sterilize the portion of the room only when the room is identified as empty by the person detector.

In one embodiment, the illumination system includes a communication interface. The communication interface may be configured to receive notifications. The processor circuitry 16 may be configured to alter a color of the emitted electromagnetic radiation based on the received notifications. For example, the illumination system may illuminate an escape route (e.g., illuminating an exit) when a fire alarm, hurricane warning, etc. is received by the communication interface.

In one embodiment, the communication interface also receives communications from nearby equipment. For example, the communication interface may identify nearby equipment using radio frequency identification (RFID) or Bluetooth. The processor circuitry 16 may modulate the emitted electromagnetic radiation based on the detected nearby equipment.

The communication interface may also receive medical information from medical monitoring equipment. The processor circuitry 16 may control the emitted electromagnetic radiation based on the received medical information. For example, the brightness of the electromagnetic radiation may be altered based on received contraction spacing (e.g., the brightness may be increased as contraction spacing decreases).

In one embodiment, the processor circuitry 16 is configured to alter a wavelength range included in the emitted electromagnetic radiation based on a time of day. For example, the wavelength range of the emitted electromagnetic radiation may be altered to include less blue light later in the day.

In one embodiment, the processor circuitry 16 controls the emitted electromagnetic radiation based on a lighting profile. The lighting profile identifies at least one of wavelengths, brightness, etc. The lighting profile may be selected based on an identified user. For example, different doctors may have different lighting profiles. The processor circuitry 16 may also identify different doctors (i.e., to select the appropriate profile) using RFID, facial recognition, Bluetooth, etc.

In one embodiment, the processor circuitry 16 controls the emitted electromagnetic radiation based on a use case. The use case may be the individuals in the room, a medical procedure, etc. For example, if the use case is for a newborn baby, the processor circuitry 16 may limit the inclusion of near-IR light in the emitted electromagnetic radiation. As another example, the illumination system may be located in a room associated with a particular medical procedure. When movement is sensed in the room, the processor circuitry 16 may implement a lighting profile associated with the medical procedure.

The illumination system 10 may include a monitoring sensor configured to monitor a performance of the illumination system 10. For example, the monitoring sensor may include at least one of a current sensor, temperature sensor, brightness sensor, or wavelength sensor. The monitoring sensor may send measured properties to the processor circuitry 16. The monitoring sensor may be configured to detect properties of the illumination system 10 (e.g., current drawn by the light source, brightness of the emitted light, temperature of the light source) to determine a status of the illumination system 10. For example, based on measured current drawn by the light source and brightness of the emitted electromagnetic radiation, the processor circuitry 16 may determine that maintenance of the light source 16 will soon be required (e.g., at least one of the light emitters 40 may soon fail).

In one embodiment, the processor circuitry 16 may alter operation of the illumination system 10 based on the properties detected by the monitoring sensor. For example, the processor circuitry 16 may detect that a light emitter 40 is outputting less light 18 (i.e., the light emitter is dim). The processor circuitry 16 may compensate for the underperforming light emitter 40 by relying on neighboring light emitter 40 (e.g., turning on other light emitters 40 or increasing light generation from the neighboring light emitters 40).

The processor circuitry 16 may identify potential issues by monitoring properties of the components using the monitoring sensor. For example, the processor circuitry 16 may identify a change in monitoring properties from previous readings as a sign of current or future component failure.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A medical illuminating system for illuminating a work area, the system comprising:

a light source configured to emit light and including optical components configured to modulate properties of a spot size of the emitted light;

a mount configured to mechanically support and maintain a position of the light source;

processor circuitry configured to modulate properties of the spot size defining an area illuminated by the emitted light, by controlling the optical components; and a distance sensor configured to measure the working distance wherein: the processor circuitry is further configured to compensate for a working distance of the light source by maintaining an area of the spot size, a brightness of the spot size, and a position of the spot size by modulating the properties of the spot size by controlling the optical components such that the properties of the spot size are independent of the measured working distance.

2. The system of claim 1, further comprising a photodetector configured to measure properties of at least one of:

the spot size including at least one of the position, the brightness, the area, or the pattern of the spot size; or the ambient light brightness by measuring a brightness of a location outside of the illuminated area.

3. The system of claim 2, wherein the processor circuitry is configured to:

detect an illumination anomaly comprising at least one of a glare or a shadow based on an output of the photodetector;

modulate properties of the light source, such that the detected illumination anomaly is mitigated.

4. The system of claim 2, wherein the processor circuitry is configured to modulate the brightness of the emitted light based on the ambient light brightness, such that a higher ambient light brightness corresponds to a higher brightness of the illuminated area.

5. The system of claim 2, wherein the processor circuitry is configured to modulate the brightness of the emitted light, such that the measured brightness falls within a desired brightness range.

6. The system of claim 1, wherein:

the processor circuitry is configured to send control signals to the optical components of the light source; and the optical components are further configured to modulate the properties of the spot size based on the control signals received from the processor circuitry.

7. The system of claim 1, wherein:

the light source includes light emitters located at different spatial positions; and the processor circuitry is further configured to control the properties of the spot size without mechanical movement of the light source by controlling properties of the light emitted by the light emitters.

8. The system of claim 1, wherein:

the light source includes a mask configured to reduce transmission of the light within a region of the illuminated area referred to as a masked region; and the processor circuitry is configured to control at least one of the location, size, or shape of the masked region.

9. The system of claim 8, wherein the mask comprises a liquid crystal filter.

10. The system of claim 1, wherein the light source is a laser source.

11. The system of claim 1, wherein the optical components include at least one of a focus mechanism, an aperture, a diffraction grating, a mask, or a lens.

12. The system of claim 1, wherein the mount includes an actuator configured to control a position of the illuminated area by adjusting at least one of a position or an angle of at least one of the light source or the optical components.

13. The system of claim 1, further comprising a remote control configured to send remote control signals to the processor circuitry, wherein:

the remote control signals include at least one of a measurement location based on a location of the remote control or a measured brightness at the measurement location;

the processor circuitry is further configured to:

control the position of the illuminated area, such that a center of the illuminated area has a defined position relative to the location of the measurement location; or control the brightness of the illuminated area, such that the measured brightness at the measurement location.

14. The system of claim 13, wherein:

the remote control signals include multiple measurement locations;

the processor circuitry is configured to modulate properties of the light source, such that a brightness at each of the multiple measurement locations falls within the desired brightness range.

15. The system of claim 14, wherein the modulated properties of the light source include at least one of position, focus, and brightness of the illuminated area.

16. The system of claim 1, wherein the processor circuitry is further configured to control wavelengths contained in the emitted light based on a received color profile.

* * * * *